United States Patent
Shimoyama et al.

(10) Patent No.: US 9,845,439 B2
(45) Date of Patent: *Dec. 19, 2017

(54) METHOD FOR BLENDING COALS FOR COKEMAKING AND METHOD FOR PRODUCING COKE

(71) Applicant: JFE STEEL CORPORATION, Chiyoda-ku, Tokyo (JP)

(72) Inventors: Izumi Shimoyama, Fukuyama (JP); Takashi Anyashiki, Kawasaki (JP); Kiyoshi Fukada, Fukuyama (JP); Hidekazu Fujimoto, Kawasaki (JP); Tetsuya Yamamoto, Fukuyama (JP); Hiroyuki Sumi, Kawasaki (JP)

(73) Assignee: JFE STEEL CORPORATION, Tokyo (JP)

( * ) Notice: Subject to any disclaimer, the term of this patent is extended or adjusted under 35 U.S.C. 154(b) by 517 days.

This patent is subject to a terminal disclaimer.

(21) Appl. No.: 14/387,742

(22) PCT Filed: Mar. 25, 2013

(86) PCT No.: PCT/JP2013/001981
§ 371 (c)(1),
(2) Date: Sep. 24, 2014

(87) PCT Pub. No.: WO2013/145679
PCT Pub. Date: Oct. 3, 2013

(65) Prior Publication Data
US 2015/0075962 A1    Mar. 19, 2015

(30) Foreign Application Priority Data
Mar. 27, 2012    (JP) .................. 2012-071515

(51) Int. Cl.
*C10L 5/04* (2006.01)
*C10B 57/04* (2006.01)
(Continued)

(52) U.S. Cl.
CPC ............... *C10L 5/04* (2013.01); *C10B 57/04* (2013.01); *C10L 9/10* (2013.01); *G01N 33/222* (2013.01);
(Continued)

(58) Field of Classification Search
CPC .. C10B 57/04; C10L 2290/24; C10L 2290/60; C10L 2300/20; C10L 5/04; C10L 9/10; G01N 33/222
See application file for complete search history.

(56) References Cited

U.S. PATENT DOCUMENTS 9,463,980 B2 * 10/2016 Fukada .................. C10B 57/04

FOREIGN PATENT DOCUMENTS

JP    8-176553 A    7/1996
JP    09-255966    9/1997
(Continued)

OTHER PUBLICATIONS

Korean Grant to Patent for KR 2014-7026669 issued Feb. 26, 2016.
(Continued)

*Primary Examiner* — Renee Robinson
*Assistant Examiner* — Derek Mueller
(74) *Attorney, Agent, or Firm* — RatnerPrestia

(57) ABSTRACT

Provided is a technique by which the compatibility between coals for cokemaking can be quantitatively determined to estimate the coke strength taking into account the compatibility and to select and blend coals based on the coke strength estimated taking into account the compatibility, thereby allowing the production of a coke with the desired strength. A method for blending coals for cokemaking (Continued)

includes predicting the strength of a coke to be produced from a blend of a plurality of coals based on a difference between the surface tensions of the plurality of coals after heat treatment and determining the types and proportions of the coals to be blended.

10 Claims, 3 Drawing Sheets

(51) Int. Cl.
*G01N 33/22* (2006.01)
*C10L 9/10* (2006.01)
(52) U.S. Cl.
CPC ....... *C10L 2290/24* (2013.01); *C10L 2290/60* (2013.01); *C10L 2300/20* (2013.01)

(56) References Cited

FOREIGN PATENT DOCUMENTS

| JP | 2002348111 A | 12/2002 |
|---|---|---|
| JP | 2005-281355 A | 10/2005 |
| JP | 2008-069258 A | 3/2008 |
| WO | WO 2012/029983 A1 | 3/2012 |

OTHER PUBLICATIONS

English Translation of Korean Grant to Patent for KR 2014-7026669 issued Feb. 26, 2016.
Japanese Office Action for Japanese Application No. 2014-507420, dated Sep. 2, 2014, including Concise Statement of Relevance of Office Action, 4 pages.
Supplementary European Search Report dated Mar. 12, 2015, application No. EP 13 76 7265.
Maggi Forrest et al: "Theoretical and Experimental Approaches to the Carbonization of Coal and Coal Blends", Nov. 12, 1982, American Chemical Society, vol. 205, pp. 1-25.
Myongsook, S. Oh et al: "An Experimental and Modeling Study of Softening Coal Pyrolysis", Aiche Journal, vol. 35, No. 5, May 1, 1989, pp. 775-792.
P.S. Dash et al: "Laboratory Scale Investigation on Maximising Utilisation of Carbonaceous inerts in Stamp Charging to Improve Coke Quality and Yield", vol. 34, No. 1, Jan. 1, 2007, pp. 23-29.
International Search Report dated May 7, 2013, application No. PCT/JP2013/001981.

\* cited by examiner

METHOD FOR BLENDING COALS FOR COKEMAKING AND METHOD FOR PRODUCING COKE

CROSS REFERENCE TO RELATED APPLICATIONS

This is the U.S. National Phase application of PCT/JP2013/001981, filed Mar. 25, 2013, which claims priority to Japanese Patent Application No. 2012-071515, filed Mar. 27, 2012, the disclosures of each of these applications being incorporated herein by reference in their entireties for all purposes.

FIELD OF THE INVENTION

The present invention relates to a method for blending coals for cokemaking based on an estimate of the strength of the coke to be produced from a coal blend of different brands of coals to produce a coke with high strength, and also relates to a method for producing a coke with high strength from an optimal coal blend.

BACKGROUND OF THE INVENTION

It is widely known that a coke with high strength is desirable for use as a raw material in the production of pig iron in a blast furnace. A coke with low strength would disintegrate in a blast furnace and thus decrease the gas permeability of the blast furnace, which leads to unstable production of pig iron.

In the production of metallurgical coke by the carbonization of coal in a horizontal chamber coke oven, the strength of the resulting coke depends on the conditions such as the method for selecting coals, the method for preparation, the carbonization conditions, the quenching conditions, and the post-treatment conditions. Among these conditions, conditions related to the equipment and operation are difficult to change drastically because of equipment constraints; therefore, the selection of coals is considered the most important factor in controlling the coke properties.

Various methods are known for blending coals to produce a coke with the desired strength, including the method discussed in Non Patent Literature 1. All of these methods involve predicting the strength of the resulting coke based on the properties of the coals to be blended and determining a blend of coals predicted to provide high strength.

It is known, however, that the conventional methods for blend determination often provide inaccurate estimation of coke strength. One example is the effect known as "coal compatibility". For example, as disclosed in Patent Literature 1, it is known that additivity is not necessarily present between the strength of a coke produced from a coal blend and the strength of a coke produced from each coal to be blended. Although various studies have been made to identify the cause of the "compatibility" effect, no technique has been available that allows reliable "compatibility" prediction to determine a combination of coals with good "compatibility".

PATENT LITERATURE

PTL 1: Japanese Unexamined Patent Application Publication No. 9-255966

NON PATENT LITERATURE

NPL 1: Miyazu et al., "Nippon Kokan Technical Report", Vol. 67(1975), p. 1

SUMMARY OF THE INVENTION

As discussed above, the coal compatibility has not been well understood, and the strength of a coke produced from a coal blend often falls below the predicted strength. The technique disclosed in Patent Literature 1 lacks simplicity because it needs to experimentally determine the compatibility for each of numerous combinations of coals. In addition, the compatibility estimation in Patent Literature 1 uses the parameters used in the methods for coke strength estimation known in the art, including the maximum fluidity (MF), the mean maximum reflectance ($R_O$), and the total reactive (TR). These parameters are insufficient to evaluate the compatibility effect, which cannot be explained by the methods known in the art.

In view of the foregoing background, it is an object of the present invention to provide a technique by which the compatibility between coals for cokemaking can be quantitatively determined to estimate the coke strength taking into account the compatibility and to select and blend coals based on the coke strength estimated taking into account the compatibility, thereby allowing the production of a coke with the desired strength.

The inventors have conducted extensive research to solve the foregoing problem. As a result, the inventors have found that the compatibility between coals for cokemaking is well expressed by the surface tensions of the coals after heat treatment. As used herein, the term "coal after heat treatment" refers to a coal heated to 350° C. to 800° C. in an inert gas atmosphere and then cooled in an inert atmosphere, which is hereinafter also referred to as "semicoke". The term "coal compatibility" refers to how suitable the combination of the coals to be blended is. In the present invention, a combination of coals with good compatibility is defined as a combination of coals that produces a coke with increased or substantially the same strength, whereas a combination of coals with poor compatibility is defined as a combination of coals that produces a coke with decreased strength.

Based on the foregoing discovery, the present invention includes the following aspects.

[1] A method for blending coals for cokemaking, comprising:
blending a plurality of coals to prepare a coal blend for use in cokemaking;
determining types and blending ratios of the coals to be blended based on a difference between surface tensions of the plurality of coals after heat treatment.

[2] The method for blending coals for cokemaking according to [1], comprising:
blending a mixture of plural coals with additional coal for cokemaking,
selecting the additional coal such that the difference between the surface tension of the coal mixture of the plural coals after heat treatment and the surface tension of the additional coal after heat treatment is 1.5 mN/m or less.

[3] The method for blending coals for cokemaking according to [1], wherein the plurality of coals are selected and blended such that the surface tensions of all of the plurality of coals after heat treatment fall within the range of (average−1.5) mN/m to (average+1.5) mN/m, where average is the average surface tension of the coals after heat treatment.

[4] The method for blending coals for cokemaking according to [1] or [3], wherein the plurality of coals are blended such that the absolute difference between the surface tension of all the coals that accounts for 70% by mass or more in total in the plurality of coals after heat treatment and the average surface tension of all of the coals after heat treatment falls within the range of 0.8 mN/m or less.

[5] The method for blending coals for cokemaking according to [1] to [4], wherein the plurality of coals are blended such that a total surface tension difference S determined from the surface tensions of the plurality of coals that constitute the coal blend after heat treatment and the blending ratios of the coals is 1.0 mN/m or less, the total surface tension difference S being determined by equation (1):

[Math. 1]

$$S = \sum_{i=1}^{n} \sum_{j=1}^{n} w_i w_j \Delta \gamma_{ij} \quad (1)$$

where $w_i$ and $w_j$ are the blending ratios of an i-th coal and a j-th coal, respectively, $\Delta\gamma_{ij}$ is the absolute surface tension difference between the i-th coal and the j-th coal after heat treatment, and n is the number of coals to be blended.

[6] A method for producing a coke, comprising carbonizing the coals blended by the method for blending coals for cokemaking according to any one of [1] to [5] to produce a coke.

The present invention can also be practiced as follows.

[7] A method for estimating coke strength includes measuring the surface tensions of a plurality of coals and predicting the strength of a coke to be produced from a blend of the plurality of coals based on a difference between the measured surface tensions of the coals.

[8] A method for blending coals for cokemaking includes measuring the surface tensions of a plurality of coals, predicting the strength of a coke to be produced from a blend of the plurality of coals based on a difference between the measured surface tensions of the coals, and determining the coals to be blended such that the coke to be produced has a higher strength.

[9] A method for blending coals for cokemaking includes blending a coal or a blend or a plurality of coals with another coal for cokemaking. The other coal is selected such that the difference between the surface tension of the coal or the blend of the plurality of coals and the surface tension of the other coal is 1.5 mN/m or less.

[10] A method for blending coals for cokemaking includes blending a plurality of coals such that the absolute difference between the surface tension of a coal that accounts for 80% by mass or more of the coal blend of the plurality of coals falls within the range of 3.0 mN/m or less.

[11] A method for selecting coals for cokemaking includes measuring the surface tensions of a plurality of coals, predicting the strength of a coke to be produced from a blend of the plurality of coals based on a difference between the measured surface tensions of the coals, and selecting coals such that the coke to be produced has a higher strength.

[12] In the method for estimating coke strength according to Item [7], the surface tensions of the coals are measured after heat treatment.

[13] In the method for blending coals for cokemaking according to any one of Items [8] to [10], the surface tensions of the coals are measured after heat treatment.

[14] In the method for selecting coals for cokemaking according to Item [11], the surface tensions of the coals are measured after heat treatment.

[15] A method for producing a coke includes carbonizing the coals blended by the method for blending coals for cokemaking according to any one of Items [8], [9], [10], and [13] to produce a coke.

According to the present invention, the compatibility between coals used as raw materials can be quantitatively evaluated based on their surface tensions. Thus, the present invention allows accurate prediction of the strength of the coke to be produced from a blend of a plurality of cokes. In addition, the present invention allows the coals to be blended to be selected and determined such that the coke to be produced has a higher strength. Furthermore, the present invention allows the production of a coke with high strength.

DETAILED DESCRIPTION OF EMBODIMENTS OF THE INVENTION

Figure 1:
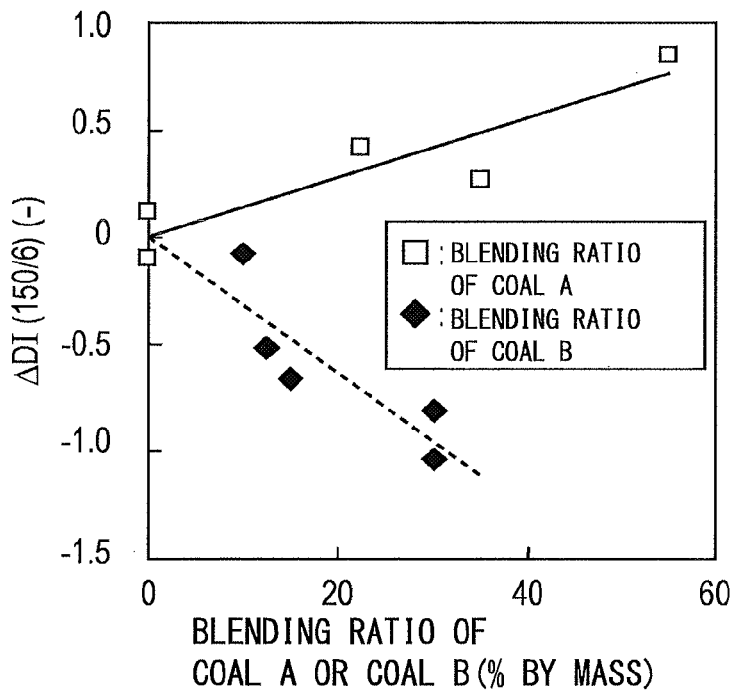
FIG. 1 is a graph showing variations in the coke strength of coal blends containing coal A, which has a smaller surface tension difference, and coal B, which has a larger surface tension difference.

It is commonly known that polar solvents dissolve polar materials well, whereas non-polar solvents dissolve non-polar materials well. Similarly, two different types of solid materials closer in their chemical properties (e.g., surface tension) adhere more strongly to each other. During the coking of coal, it melts and then solidifies into coke with heating. During this process, different coals need to adhere to each other to form a strong coke structure.

It is believed in the art that this adhesion structure is formed by the fusion bonding of coals and that the coal plasticity (e.g., Gieseler maximum fluidity MF) plays an important role. In contrast, the inventors have focused on the phenomenon by which different types of coals adhere to each other and have conducted research thereon, assuming that the strength of this adhesion also has some influence on the coke strength. As a result, the inventors have experimentally demonstrated the relationship between the surface tension difference and the coke strength.

To investigate the above adhesion phenomenon, it would be desirable to actually measure and use the surface tension of coal plastic at temperatures at which the coal softens (350° C. to 550° C.). However, no method has been known to measure the surface tension at such high temperatures. Accordingly, the inventors have researched various alternative methods and consequently have found that the adhesion strength between coals is well expressed by the surface tensions of the coals after heat treatment at temperatures of the softening temperature of the coals or more and the coking temperature or less, i.e., 350° C. to 800° C., and cooling to room temperature, preferably the surface tensions after rapidly quenching to room temperature, and that their adhesion phenomenon affects the coke strength. The inventors have also found that the above surface tensions can be estimated from the surface tensions of coals.

Specifically, the inventors have found that a coke produced from a blend of different types of coals tends to have a higher strength as semicokes prepared from these coals by heat treatment have a smaller surface tension difference and that the coke tends to have a lower strength as the semicokes have a larger surface tension difference. This novel discovery has led to the present invention. The present invention will now be described in detail.

The surface tensions of coals or heat-treated coals can be measured by a known method such as film flotation (see D. W. Fuerstenau, International Journal of Mineral Processing, vol. 20(1987), p. 153). This method can be applied to either coals or heat-treated coals (semicokes) and allows their surface tension distribution to be determined from a finely crushed sample. As used herein, the term "film flotation" refers to a method for surface tension measurement based on the assumption that crushed sample particles falling from a gas phase onto a surface of a liquid have the same surface tension as the liquid if the sample particles sink in the liquid (if the sample particles have a contact angle of substantially 0°). The surface tension distribution of a sample can be determined by allowing sample particles to fall onto various liquids with different surface tensions, determining the mass proportion of sample particles floating on each liquid, and plotting the results as a frequency distribution curve.

The average of the resulting surface tension distribution can be used as the representative surface tension of the sample. The average of the surface tension distribution of each sample is hereinafter referred to as the surface tension of the sample. Alternatively, the representative surface tension may be defined taking into account the surface tension distribution (e.g., the standard deviation of the distribution). If a heat-treated coal is used as a sample for surface tension measurement, the heat treatment temperature is preferably set to the softening temperature range of the sample.

The surface tension measurement by film flotation is preferably performed as follows. The liquids used in film flotation may be liquids having surface tensions of 20 to 73 mN/m, which is the range of the surface tension distribution of coals and softened coals. For example, the liquids having surface tensions of 20 to 73 mN/m may be prepared from an aqueous solution of an organic solvent such as ethanol, methanol, propanol, tert-butanol, or acetone. In view of the measurement principle described above, it is desirable to measure the surface tension at a contact angle of substantially 0°. Accordingly, a sample having a smaller particle size is preferred for the surface tension measurement because crushed sample particles having a larger particle size have a larger contact angle. However, sample particles having a particle size of less than 53 µm tend to aggregate. To prevent aggregation, the particle size of the sample particles is preferably adjusted to 53 to 150 µm.

As an example of a method for preparing a semicoke sample from a coal by heat treatment, the following conditions are preferred. A coal is crushed to a particle size of 200 µm or less, is heated to 500° C. at 3° C./min in an inert gas atmosphere, is quenched with liquid nitrogen, is crushed to a particle size of 150 µm or less, and is dried at 120° C. in a dry inert gas stream for 2 hours. To prepare a homogeneous sample from a coal with uneven maceral composition and properties, the coal is preferably crushed to a particle size of 250 µm or less, which is the particle size of a crushed coal used in coal proximate analysis according to JIS M8812. Although the heating rate is set to 3° C./min because the heating rate for the production of coke in a coke oven is about 3° C./min, it is desirable to change the heating rate depending on the heating rate for the production of the coke to be evaluated by surface tension. The coal is preferably heated in an inert gas atmosphere, which prevents change in quality due to the reaction between the coal and the gas. Examples of inert gases include gases that do not react with the coal during heating, such as nitrogen, helium, and argon. The heating temperature (maximum temperature during heat treatment) is preferably within the temperature range from 350° C., at which the coal starts softening, to 800° C., at which coking completes. In particular, a heat treatment temperature around 500° C. is preferred because coals commonly used in cokemaking have softening temperatures about 350° C. to 550° C. and their adhesion structure is fixed at 480° C. to 520° C. After heating, the coal is preferably cooled in an inert gas atmosphere. This prevents the reaction between the coal and the gas during cooling. To cool the coal while maintaining the molecular structure thereof in a heated state, the coal is preferably quenched at 10° C./rain or higher. The coal may be dried in any manner that allows moisture to be removed from the surface thereof. For example, the coal may be dried by heating to 100° C. to 200° C. in an inert gas, such as nitrogen or argon, or may be dried under reduced pressure.

The surface tensions of the coals used as raw materials for cokemaking are determined in advance by the method described above for each brand (type). To determine the compatibility between two types of coals, the surface tension difference between semicokes prepared from the coals by heat treatment is calculated. The two types of coals are determined to have poor compatibility if they have a large surface tension difference and are determined to have good compatibility if they have a small surface tension difference. Research on various blends has shown that a surface tension difference between two types of coals of 1.5 mN/m or more results in a significant decrease in the strength of the resulting coke. This value, i.e., 1.5 mN/m, can be used as a threshold for compatibility determination.

To determine the compatibility from the surface tensions of coals after heat treatment, it is most desirable to compare the surface tensions of the coals after heat treatment at the same temperature, although it may be determined from the average surface tension over a certain temperature range. Alternatively, the surface tensions of the coals at their respective softening characteristic temperatures (e.g., the maximum fluidity temperatures, the initial softening temperatures, or the solidification temperatures) may be compared. To evaluate the compatibility between a certain coal and a blend of two or more types of coals, the surface tension of a semicoke prepared from the blend of two or more types of coals may be a measured surface tension of the semicoke of the blend or may be the average surface tension of semicokes prepared from the coals in the blend (preferably, the weighted average taking into account the composition).

In this manner, the compatibility between coals can be quantitatively evaluated. The coke strength can then be predicted based on the evaluation. This can be performed, for example, by adding a correction term including the surface tension to a formula for strength prediction known in the art. Based on the compatibility evaluation, it is possible to select desired coal brands and to determine the blending ratios thereof so that the coke to be produced has high strength. A coal blend of the thus-selected coal brands can be carbonized to produce a coke with high strength. The target coke strength may be determined, for example, from the capacity and operating conditions of the blast furnace.

The strength of the coke to be produced by carbonizing a coal blend of a plurality of coals is preferably predicted from the following parameter based on the surface tension difference. Specifically, if a coal blend contains n types of coals, the blending ratio of each coal is denoted as $w_i$ (which refers to the blending ratio of the first, second, . . . , i-th, . . . , or n-th coal). The proportion of the j interface formed by the i-th coal and the j-th coal is expressed as the product of the blending ratios $w_i$ and $w_j$. If the absolute surface tension difference between the i-th coal and the j-th coal is denoted as $\Delta\gamma_{ij}$, the parameter S for the surface tension difference between the coals to be blended can be represented by equation (1):

[Math. 1]

$$S = \sum_{i=1}^{n} \sum_{j=1}^{n} w_i w_j \Delta\gamma_{ij} \qquad (1)$$

Research on the strength of a coke produced by carbonizing a coal blend of a plurality of coals has demonstrated that a coke with high strength can be produced by blending a plurality of coals such that the absolute differences between the surface tensions of semicokes prepared from the coals that account for 70% by mass or more of the plurality of coals by heat treatment and the average surface tension of semicokes prepared from all of the coals that constitute the coal blend falls within the range of 0.8 mN/m or less. The research has also demonstrated that coke with high strength can be produced by blending a plurality of coals such that the surface tensions of semicokes prepared from all of the coals fall within the range of ±1.5 mN/m from the average surface tension of semicokes prepared from the coals by heat treatment. The average surface tension of semicokes prepared from all of the coals that constitute the coal blend is preferably determined as the average surface tension of semicokes prepared from the coals weighted by the blending ratios of the coals.

The surface tension difference also affects the interfacial tension of adhesion interfaces. Qualitatively, the adhesion strength of an interface between two types of materials is affected by the interfacial tension thereof, and a larger interfacial tension results in a lower adhesion strength. Accordingly, the interfacial tension may be used instead of the surface tension difference. Whereas the interfacial tension between two types of materials can be measured, a method is also known for estimating the interfacial tension from the surface tension of each material. Thus, instead of simply determining the surface tension difference, the interfacial tension may be determined based on a more precise estimation theory and may be used to perform similar compatibility estimation.

Although the present invention is applied to coal, which is a major raw material for cokemaking, in the example described above, it is also theoretically possible to apply the present invention to other raw materials such as oil coke, pitch, and other organic materials.

As described above, the compatibility between coals for cokemaking is clearly indicated by the surface tension difference between semicokes prepared from the coals by heat treatment. Based on this knowledge, one can make the following decisions. For example, one can select and purchase coal brands having good compatibility with other coal brands currently used and thus predicted to produce a coke with high strength in cokemaking. In addition, one can sell coals to customers who use brands having good compatibility with those coals so that they can produce a coke with high strength at their plant. When coals are used, a combination of coals with the highest possible compatibility (close surface tensions) can be used to produce a coke with high strength. The surface tension difference can be used as a parameter to more accurately predict the strength of the coke to be produced from the coal blend. This allows coke strength control with improved precision and also contributes to stable blast furnace operation.

Thus, the use of the surface tensions of coals or heat-treated coals enables quantitative coal compatibility evaluation, which cannot be performed by the methods known in the art. This provides the advantage of allowing effective selection of the coals to be purchased and used.

EXAMPLE 1

Coals for use in cokemaking were used as samples. Each of the coals was crushed to a particle size of 200 μm or less and was charged into a graphite vessel. The vessel was heated to 500° C. at 3° C./rain in an electric furnace in an inert gas atmosphere (nitrogen) and was quenched by dipping in liquid nitrogen. The resulting semicoke was crushed to a particle size of 150 μm or less and was dried at 120° C. in a dry inert gas stream for 2 hours to prepare a semicoke sample for surface tension measurement. The surface tension distribution of each sample was measured by film flotation. The heating rate was set to 3° C./min because the heating rate for the production of coke in a coke oven is about 3° C./min. The liquid used in the surface tension measurement by film flotation was an aqueous ethanol solution, which is inexpensive and is easy to handle. The representative surface tension of the sample was determined as the average of the surface tension distribution measured by film flotation.

A base coal blend was prepared by blending five coal brands. The surface tension of the coal blend was measured to be 40.1 mN/m, and the weighted average surface tension of the coal brands was 40.2 mN/m. In addition to the base coal blend, coal A, which had a surface tension of 40.1 mN/m, and coal B, which had a surface tension of 37.5 mN/m, were obtained, which were not contained in the coal blend.

The base coal blend was blended with coal A or coal B in varying proportions to prepare coal blends. The content of particles with particle sizes of 3 mm or less in the coal blends was adjusted to 100% by mass, and the moisture content was adjusted to 8% by mass. Sixteen kilograms of each coal blend was compacted to a bulk density of 750 kg/m$^3$ and was carbonized in an electric furnace. After the compact was carbonized at a furnace wall temperature of 1,100° C. for 6 hours, it was cooled with nitrogen and was tested for their drum index. The drum index DI150/6 was determined by charging a coke having a particle size of 25 mm or more into a predetermined drum tester in accordance with the drum strength measurement method in JIS K2151, rotating the drum 150 revolutions at a rotational speed of 15 rpm, measuring the mass proportion of a coke having a particle size of 6 mm or more, and calculating the percentage thereof in the charge mass. The differences (ΔDI) between the strengths (index DI150/6) of the resulting cokes and the strength of a coke produced from the base coal blend alone are shown in FIG. 1. The coal blends containing coal A or coal B contained base coal blends with slightly different compositions so that the coal blends containing coal A or coal B had a weighted average mean maximum vitrinite reflectance (mean Ro) of 1.01% and a weighted average Gieseler plastometer maximum fluidity (log MF) of 2.35 (in log(MF/ddpm)). Although the surface tension of the base coal blend varied slightly as the blend composition thereof varied slightly, it fell within the range of ±0.5 mN/m from the above surface tension of the base coal blend. The blending ratio of coal A or coal B is relative to the total amount of coal, and the balance is the base coal blend.

According to a coke strength estimation model known in the art, it is known that the coke strength is determined by the weighted average mean maximum vitrinite reflectance (mean Ro, in accordance with JIS M8816) and the weighted average common logarithm of Gieseler elastometer maximum fluidity MF (in accordance with JIS M8801) (log MF) of the coals to be blended. Hence, it is reasonable in this test to estimate that the cokes to be produced have generally similar strengths irrespective of the blending ratios of coal A and coal B. Nevertheless, FIG. 1 demonstrates that whereas the addition of coal A, which is close in surface tension to the base coal blend, resulted in relatively small variations in coke strength, the blending of coal B, which differs largely in surface tension from the base coal blend, resulted in a larger decrease in strength with increasing blending ratio.

These results clearly illustrate the "compatibility" between the coals to be blended. Specifically, coal A is determined to have good compatibility with the base coal blend (the strength does not decrease depending on the blending ratio), whereas coal B is determined to have poor compatibility with the base coal blend (the strength decreases depending on the blending ratio). Examination of the surface tension difference showed that in the coal blends containing coal A, coal A and the base coal blend had a smaller surface tension difference, whereas in the coal blends containing coal B, coal B and the base coal blend had a larger surface tension difference.

These results demonstrate that the surface tension difference serves as a parameter for the determination of the compatibility between coals.

EXAMPLE 2

Under the conditions where 30% by mass of coal B was blended in Example 1 (referred to as "blend b"), the coal (coal C) having a surface tension of 40.9 mN/m in the base coal blend was replaced with coal D, which had a surface tension of 39.1 mN/m (referred to as "blend b'"). Coal C and Coal D had substantially the same mean maximum vitrinite reflectance (mean Ro) and common logarithm of Gieseler plastometer maximum fluidity (log MF). Coal D was not contained in the original base coal blend.

After this replacement, the surface tension of the base coal blend was measured to be 39.4 mN/m, which was 0.7 mN/m lower than in Example 1. The surface tension difference between the base coal blend and coal B in blend b' was smaller than the surface tension difference between the base coal blend and coal B in blend b. Examination of the strength of a coke produced from blend b' showed that the strength was 0.5 point higher than that of a coke produced from blend b.

These results also demonstrate that a smaller surface tension difference between the coals to be blended results in a higher strength. From these results, it can also be concluded that the blending of coal B in Example 1 resulted in a decrease in coke strength not because coal B itself had poor properties, but because the combination of the coals had poor compatibility.

EXAMPLE 3

Examples 1 and 2 demonstrated that a larger surface tension difference between semicokes prepared from a plurality of coals by heat treatment results in a larger decrease in the strength of a coke produced by carbonizing a blend of these coals and that a larger proportion of a coal that produces a semicoke having a large surface tension difference results in a larger decrease in the strength of a coke produced from the coal blend. From these examples alone, however, it is unclear how much surface tension difference results in a significant decrease in strength.

Accordingly, the inventors researched the relationship between the surface tension difference between semicokes and the adhesion strength between coals. The coals shown in Table 1 (E to M) were selected, and the adhesion strength between two types of coals in each combination shown in Table 2 was measured by the following method:

1. Two types of coals shown in Table 2 were thoroughly blended in a mass ratio of 1:1 and were crushed to a particle size of 70 µm or less;

2. The coal blend was charged into a mold having a cavity with a diameter of 6.6 mm in a sufficient amount to form a compact having a diameter of 6.6 mm and a thickness of 2.5 mm; and 3. A load of 14 MPa was applied to the mold for 10 seconds to form a compact. Ten compacts were prepared for each type of coal blend.

The bulk density of the compacts varied depending on the coal brands, ranging from 860 to 920 kg/m$^3$. The ten compacts were placed in a packed bed of coke breeze adjusted to a particle size of 1 mm or less and were carbonized in an electric furnace. The coke breeze was packed into an iron vessel having a size of 200 mm×200 mm×H 500 mm. The compacts were carbonized to 1,000° C. at 3° C./min in a nitrogen atmosphere. After carbonization, the compacts were cooled in a nitrogen atmosphere. The compressive strength was measured with an autograph available from Shimadzu Corporation. A load was applied to each measurement sample across the thickness thereof to measure the load at break. The adhesion strength was calculated as the pressure given by dividing the load by the area of the surface of the measurement sample to which the load was applied. The compressive strengths of ten measurement samples and the areas of the surfaces of the measurement samples to which the load was applied were measured for each level, and the adhesion strength for that level was calculated as the average adhesion strength. The measurement results are shown in Table 2. Because this adhesion strength measurement method uses blends of two types of coals, the samples contain numerous interfaces between the coals. The compressive strength reflects not only the adhesion strength of these interfaces, but also the strength of a coke produced from each coal and the adhesion strength of each coal with itself. Nevertheless, it is probable that the compressive strength reflects the interfacial adhesion because the coals are finely crushed to form more interfaces and one half of the contact points between coal particles are likely to be interfaces between different types of coals. The absolute surface tension differences ($\Delta\gamma$) between semicokes prepared from the coals are also shown in Table 2.

TABLE 1

| Coal | Ro (%) | logMF (log ddpm) | γ (mN/m) |
|---|---|---|---|
| Coal E | 0.71 | 1.32 | 40.2 |
| Coal F | 0.72 | 2.11 | 40.9 |
| Coal G | 0.75 | 2.28 | 40.9 |
| Coal H | 0.99 | 3.08 | 41.6 |
| Coal I | 1.00 | 2.43 | 39.6 |
| Coal J | 1.03 | 2.15 | 40.1 |
| Coal K | 1.07 | 2.09 | 38.9 |
| Coal L | 1.26 | 0.95 | 40.5 |
| Coal M | 1.62 | 1.28 | 37.8 |

TABLE 2

| Combination of coals | Adhesion strength (MPa) | Δγ (mN/m) |
|---|---|---|
| E-K | 64 | 1.3 |
| E-M | 37 | 2.4 |
| F-I | 135 | 1.3 |
| F-M | 35 | 3.1 |
| G-I | 125 | 1.3 |
| H-L | 174 | 1.1 |
| I-J | 144 | 0.5 |
| I-K | 88 | 0.7 |
| I-M | 57 | 1.8 |
| K-M | 68 | 1.1 |

Figure 2:
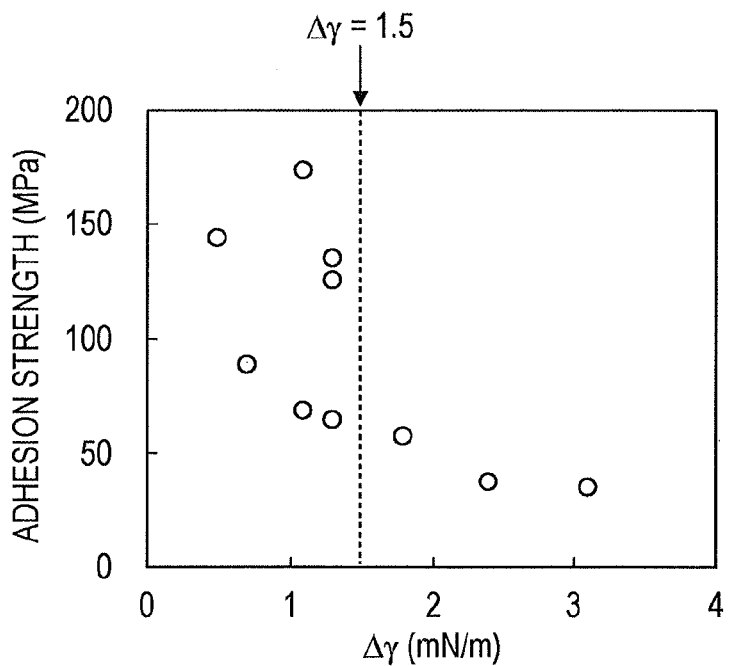
FIG. 2 is a graph showing the relationship between the surface tension difference ($\Delta\gamma$) (mN/m) between coals and the adhesion strength (MPa).

FIG. 2 is a graph showing the relationship between the surface tension difference (Δγ) (mN/m) between the coals and the adhesion strength (MPa). As shown in FIG. 2, smaller surface tension differences Δγ between two semicokes resulted in higher strengths and therefore better adhesions between two types of coals, whereas the combinations having larger surface tension differences had lower adhesion strengths. In particular, the combinations of coals with low MF (combinations of two types of coals with an average log MF of generally 2 or less) showed a strong correlation between the surface tension difference and the compressive strength. The above tendency appeared noticeably presumably because coals with low MF form a coke such that molten coals simply contact each other rather than form a coke such that molten coals fuse together to form interfaces. As can be seen from FIG. 2, surface tension differences Δγ of more than 1.5 resulted in a significant decrease in strength. This demonstrates that a decrease in strength can be prevented if a certain coal is blended with another coal such that semicokes prepared from both coals have a surface tension difference of 1.5 mN/m or less.

EXAMPLE 4

Next, a preferred method for producing a coke with high strength by blending different coal brands using the method for compatibility evaluation based on the surface tension difference was researched. To prepare a coal blend of different coal brands with a small surface tension difference, the coals may be selected such that the surface tensions thereof fall between certain upper and lower limits.

The 13 types of coals shown in Table 3 were used to prepare 4 types of coal blends having substantially the same mean maximum vitrinite reflectance Ro and common logarithm of Gieseler maximum fluidity log MF. These coal blends were carbonized in the same manner as in Example 1, and the resulting cokes were examined for their strength. In this example, the coke strength was measured in accordance with JIS K2151 as the strength index DI150/15, which was calculated from the mass of a coke having a particle size of 15 mm or more measured after a drum charged with a coke was rotated 150 revolutions. The coke strength after $CO_2$ reaction CSR was also determined in accordance with ISO 18894. CSR showed the same tendency as DI. The surface tensions of semicokes prepared from the coals in Table 3 were determined in the same manner as in Example 1. The Ro and log MF of each coal blend were determined as the average mean Ro and log MF of the coals used for blending weighted based on the blending ratios thereof. The average surface tension $\gamma_{ave}$ of each coal blend was determined as the average surface tension of semicokes prepared from the coals weighted based on the blending ratios thereof.

To determine the preferred range of surface tension, upper and lower limits were set at a predetermined distance away upward and downward from the average surface tension ($\gamma_{ave}$) of semicokes prepared from the coals that constituted a coal blend. The relationship was examined between the blending ratio of coals that produce semicokes having a surface tension between the upper and lower limits and the strength of the coke produced from the coal blend.

Figure 3:
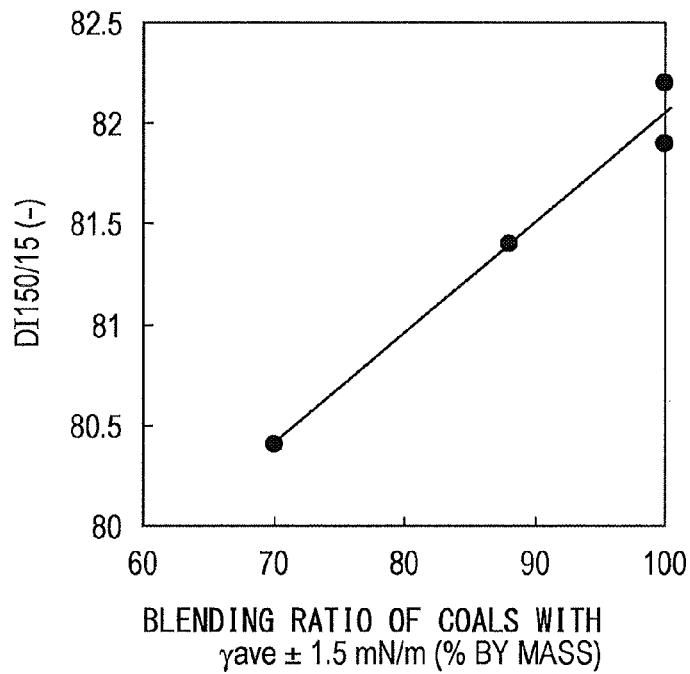
FIG. 3 is a graph showing the relationship between the blending ratio of coals that produce semicokes having a surface tension of $\gamma_{ave}$+1.5 (mN/m) to $\gamma_{ave}$−1.5 (mN/m) and the coke strength.

FIG. 3 shows the relationship between the blending ratio of coals that produce semicokes having a surface tension of $\gamma_{ave}+1.5$ (mN/m) to $\gamma_{ave}-1.5$ (mN/m) (also shown in Table 3) and the coke strength. As can be seen from FIG. 3, blending coals such that semicokes prepared from all of the coals have a surface tension of $\gamma_{ave}+1.5$ (mN/m) to $\gamma_{ave}-1.5$ (mN/m) prevents a decrease in strength due to coal compatibility and thus allows the production of a coke with high strength.

Figure 4:
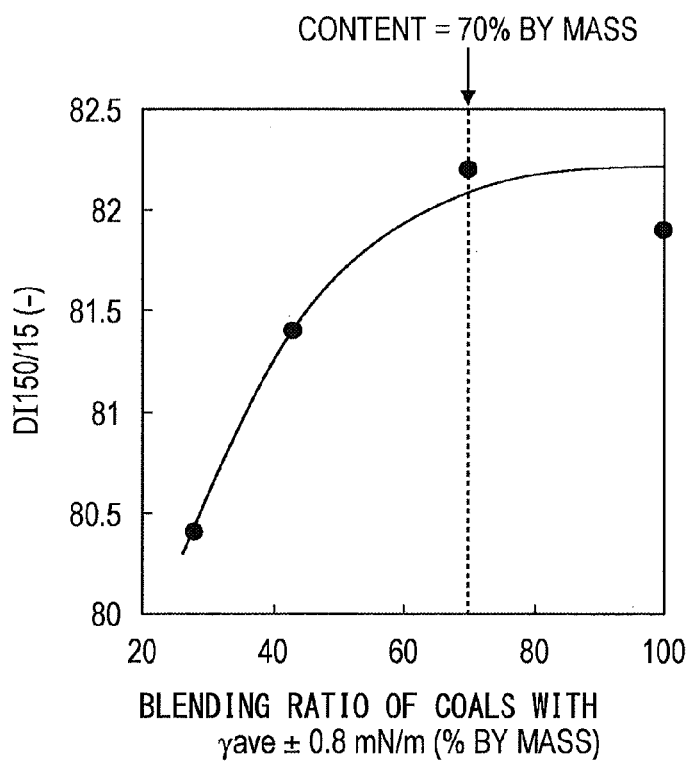
FIG. 4 is a graph showing the relationship between the blending ratio of coals that produce semicokes having a surface tension of $\gamma_{ave}$+0.8 (mN/m) to $\gamma_{ave}$−0.8 (mN/m) and the coke strength.

Example 1, however, suggests that a small proportion of a coal having a large surface tension difference results in only a slight decrease in strength. Accordingly, to determine the upper limit of the blending ratio of coals having a large surface tension difference from the average surface tension ($\gamma_{ave}$), the relationship was examined between the blending ratio of coals that produce semicokes having a surface tension of $\gamma_{ave}+0.8$ (mN/m) to $\gamma_{ave}-0.8$ (mN/m) (also shown in Table 3) and the coke strength. The results are shown in FIG. 4. As can be seen from FIG. 4, blending coals such that semicokes prepared from the coals that account for 70% by mass or more of the coal blend have a surface tension of $\gamma_{ave}+0.8$ (mN/m) to $\gamma_{ave}-0.8$ (mN/m) prevents a decrease in strength due to coal compatibility and thus allows the production of a coke with high strength. That is, if the coals that account for 70% by mass or more of the coal blend have a surface tension close to the average surface tension, a coke with high strength can be successfully produced even if the coal blend contains about 30% by mass of a coal that deviates from the above range.

Figure 5:
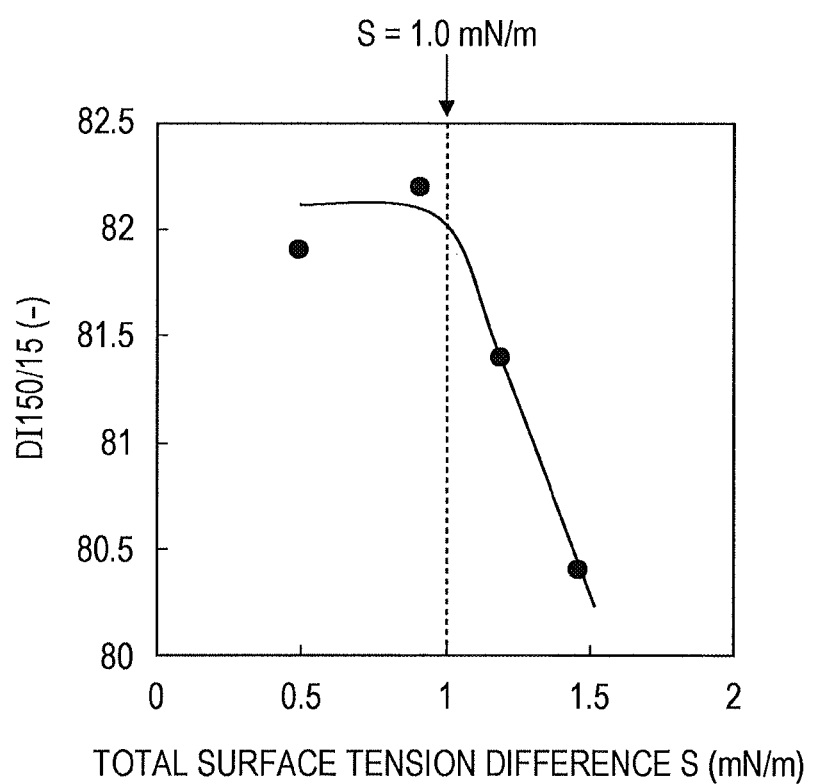
FIG. 5 is a graph showing the relationship between the total surface tension difference S between semicokes and the coke strength.

As an alternative method for determining a coal blend based on the surface tension difference, a method using the total surface tension difference S between semicokes prepared from coal brands represented by equation (1) was examined for its preferred conditions. Table 3 also shows the total surface tension difference S determined for each blend. As can be seen from FIG. 5, which shows the relationship between the total surface tension difference S and the coke strength, a coke with high strength can be produced by determining the types and proportions of the coals to be blended such that the total surface tension difference S is 1.0 (mN/m) or less.

TABLE 3

| Coal brand | Ro (-) | logMF (logddpm) | γ (mN/m) | Blending ratio (%) Blend c | Blend d | Blend e | Blend f |
|---|---|---|---|---|---|---|---|
| Coal N | 1.29 | 1.04 | 40.6 | 28 | 18 | 12 | 12 |
| Coal O | 0.76 | 2.21 | 40.2 | 0 | 8 | 12 | 3 |
| Coal P | 0.68 | 4.11 | 41.1 | 6.5 | 0 | 0 | 0 |
| Coal Q | 0.75 | 1.82 | 40.6 | 8.5 | 0 | 0 | 0 |
| Coal R | 0.99 | 1.15 | 40.9 | 0 | 9 | 0 | 0 |
| Coal S | 0.98 | 2.88 | 40.2 | 17 | 0 | 0 | 0 |
| Coal T | 0.82 | 4.43 | 39.9 | 0 | 0 | 3 | 5 |
| Coal U | 0.98 | 3.08 | 39.6 | 0 | 5 | 20 | 20 |
| Coal V | 0.85 | 3.13 | 40.9 | 20 | 30 | 0 | 30 |
| Coal W | 0.89 | 3.59 | 39.1 | 0 | 0 | 23 | 0 |
| Coal X | 1.07 | 3.18 | 39.7 | 20 | 0 | 0 | 0 |
| Coal Y | 1.10 | 2.03 | 38.9 | 0 | 30 | 0 | 0 |
| Coal Z | 1.15 | 1.49 | 37.6 | 0 | 0 | 30 | 30 |
| Ro of coal blend (%) | | | | 1.01 | 1.01 | 1.01 | 1.01 |
| logMF of coal blend (log ddpm) | | | | 2.35 | 2.36 | 2.35 | 2.35 |
| $\gamma_{ave}$ of coal blend (mN/m) | | | | 40.44 | 40.13 | 39.09 | 39.54 |
| Blend proportion of coals with $\gamma_{ave}$ ± 1.5 (mN/m) (%) | | | | 100 | 100 | 88 | 70 |
| Blend proportion of coals with $\gamma_{ave}$ ± 0.8 (mN/m) (%) | | | | 100 | 70 | 43 | 28 |
| Total surface tension difference S (mN/m) | | | | 0.49 | 0.91 | 1.19 | 1.46 |
| Coke strength DI150/15 (-) | | | | 81.9 | 82.2 | 81.4 | 80.4 |
| Coke strength CSR (%) | | | | 64.1 | 64.5 | 63.4 | 59.7 |

EXAMPLE 5

Semicoke samples were prepared from coal α and coal β in the same manner as in Example 1 with varying heat treatment temperatures and were tested for their surface tension. The results are shown in Table 4. As can be seen from Table 4, higher heat treatment temperatures resulted in higher surface tensions in the temperature range of 350° C. or higher. However, the surface tension difference between two types of semicokes prepared at the same heat treatment temperature remained substantially constant, and the magnitude relationship between the surface tensions obtained from different coals was not changed with varying temperatures for semicoke preparation. Thus, the method according to the present invention is effective if the heat treatment temperature for semicoke preparation falls within the range of 350° C. to 800° C. In view of this dependence of surface tension on heat treatment temperature, it is desirable to treat all of the coals to be blended at substantially the same heat treatment temperature for surface tension evaluation.

TABLE 4

| | Heat treatment temperature (° C.) | | | | | |
|---|---|---|---|---|---|---|
| | 350 | 400 | 450 | 500 | 600 | 800 |
| Surface tension of semicoke of coal α (mN/m) | 31.9 | 33.0 | 35.5 | 41.1 | 45.2 | 52.3 |
| Surface tension of semicoke of coal β (mN/m) | 29.8 | 30.4 | 32.4 | 37.6 | 42.2 | 48.7 |

The invention claimed is:

1. A method for blending coals for cokemaking, comprising:
    determining a percentage of each of a plurality of coals to be blended, based on a difference between surface tensions of semicokes prepared from each of the plurality of coals; and
    blending the plurality of coals according to the percentages.
2. The method for blending coals for cokemaking according to claim 1, further comprising:
    selecting an additional coal such that the difference between the surface tension of a semicoke prepared from the additional coal and the average of surface tensions of semicokes prepared from the plurality of coal is 1.5 mN/m or less; and
    blending the additional coal with the plurality of coals.
3. The method for blending coals for cokemaking according to claim 1, wherein the surface tensions of the semicokes prepared from each of the plurality of coals fall within the range of (average−1.5) mN/m to (average+1.5) mN/m, where average is the average surface tension of all of the semicokes taken together.
4. The method for blending coals for cokemaking according to claim 1, wherein 70% or more by mass of the plurality of coals are coals whose semicokes have surface tensions differing from the average of the surface tensions of semicokes of all of the plurality of coals by 0.8 mN/m or less.
5. The method for blending coals for cokemaking according to claim 1, wherein a total surface tension difference S determined according to equation (1) is 1.0 mN/m or less:

[Math. 1]

$$S = \sum_{i=1}^{n}\sum_{j=1}^{n} w_i w_j \Delta\gamma_{ij} \quad (1)$$

where $w_i$ and $w_j$ are the percentages of an i-th coal and a j-th coal in the blend, respectively, $\Delta\gamma_{ij}$ is the absolute difference between the surface tensions of the semicokes prepared from the i-th coal and the j-th coal, and n is the number of coals in the plurality of coals.

6. A method for producing a coke, comprising carbonizing the coals blended by the method for blending coals for cokemaking according to claim 1 to produce a coke.
7. A method for producing a coke, comprising carbonizing the coals blended by the method for blending coals for cokemaking according to claim 2 to produce a coke.
8. A method for producing a coke, comprising carbonizing the coals blended by the method for blending coals for cokemaking according to claim 3 to produce a coke.

9. A method for producing a coke, comprising carbonizing the coals blended by the method for blending coals for cokemaking according to claim 4 to produce a coke.

10. A method for producing a coke, comprising carbonizing the coals blended by the method for blending coals for cokemaking according to claim 5 to produce a coke.

* * * * *